United States Patent [19]

Baron

[11] Patent Number: 5,120,499
[45] Date of Patent: Jun. 9, 1992

[54] METHOD AND SYSTEM FOR ASEPTICIZING CONTACT LENSES AND STORING DEVICE

[75] Inventor: Neville A. Baron, Secaucus, N.J.

[73] Assignee: U. V. Black Box Corporation, Line Lexington, Pa.

[21] Appl. No.: 463,451

[22] Filed: Jan. 11, 1990

[51] Int. Cl.$^5$ ............................................. A61L 2/10
[52] U.S. Cl. .................................. 422/24; 250/455.1; 250/492.1; 250/504 R
[58] Field of Search ............ 422/24; 250/455.1, 492.1, 250/504 R

[56] References Cited

U.S. PATENT DOCUMENTS 4,063,890 12/1977 Baron .

OTHER PUBLICATIONS

Gritz et al. "Ultraviolet Radiation for the Sterilization of Contact Lenses", The CLAO Journal, Oct. 1990, vol. 16, No. 4, pp. 294-298.
*Dorland's Illustrated Medical Dictionary*, 26th Ed., (Phila., W. B. Saunders Co.:1985), p. 1419.
*Reference Data for Radio Engineers*, 6th Ed., (Indianapolis, H. W. Sams & Co. Inc.:1975), Chapter 22, p. 22-1.
*IES Lighting Handbook 1981 Appli. vol.* ("Nonvisual Effects of Radiant Energy",), pp. 19-14 to 19-16, 19-39.
E. W. Nester, et al., *Microbiology*, 3rd ed., (Philadelphia, Saunders College Publ.:1983), pp. 145-146.
F. Jay, *IEEE Standard Dictionary of Electrical & Electronics Terms* 2nd Ed., (The Institute of Electrical & Electronics Engineers, Inc. New York, NY:1977), p. 752.
*Essentials of Medical Microbiology*, 2nd ed., (Philadelphia, J. B. Lippincott Co:1982), p. 126.
Fink *Standard Handbook for Electrical Engineers*, 10th ed., New York, NY, McGraw-Hill Book Co.:1968), pp. 26-38, 26-39.
Gritz, et al., Ultraviolet Radiation for the Sterilization of Contact Lenses, Dept. of Ophthalmology, U. of S. California School of Medicine, p. 1-14.
Aquasteril Literature (undated)-9 pages.

*Primary Examiner*—Robert J. Warden
*Assistant Examiner*—Lyle A. Alexander
*Attorney, Agent, or Firm*—Howson & Howson

[57] ABSTRACT

Light-transmitting contact lenses of Polymethylacrylate, Gas Permeable of Hydrogel materials may be immersed in an aqueous liquid medium contained in a storing and processing device, all of which are substantially transparent to the ultraviolet radiation spectrum. The lenses, liquid medium and storing device are all irradiated with ultraviolet radiation in a preselected frequency range, while simultaneously being subjected to ultrasonic frequency vibrations to thereby cause asepticization of lenses, liquid medium and storing device. The ultraviolet irradiation and ultrasonic vibrations are insufficient to cause detrimental molecular modification to the lenses or storing device, but does cause the formation of oxidation free radicals in the liquid medium. The unique combination of ultraviolet irradiation and ultrasonic vibration in the presence of the liquid medium containing oxidation free radicals cause rapid destruction of all microorganisms associated with the lenses, liquid medium and storing device.

13 Claims, 1 Drawing Sheet

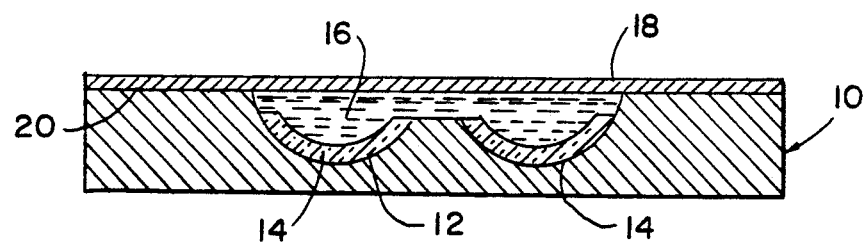
FIG. 1
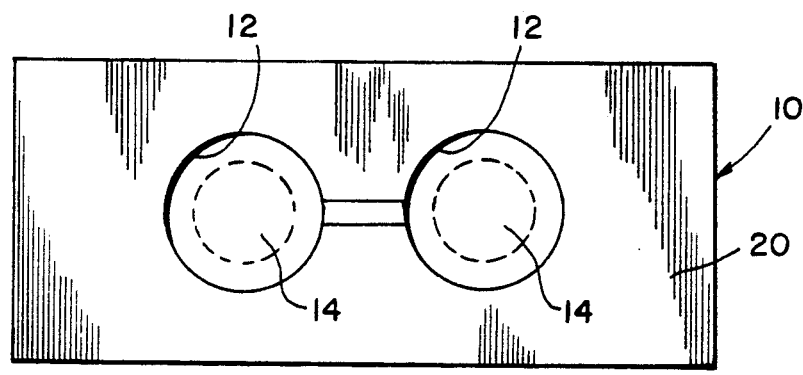
FIG. 2
FIG. 3
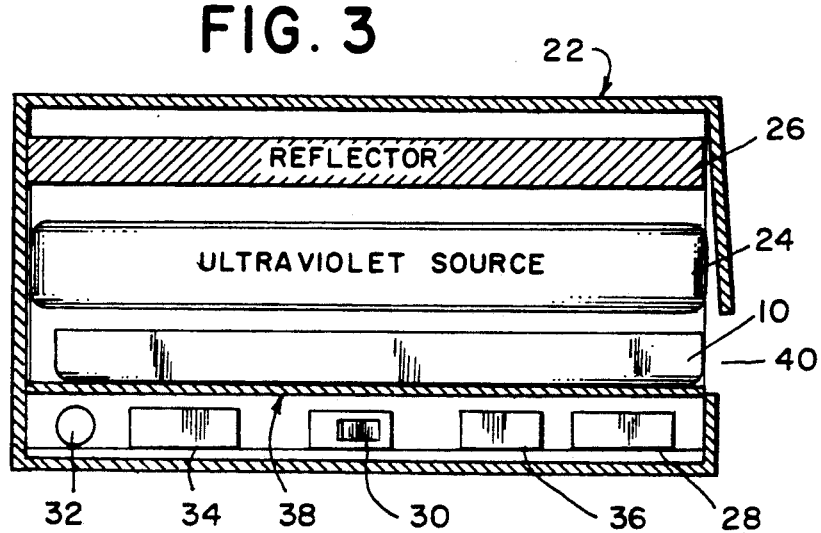

METHOD AND SYSTEM FOR ASEPTICIZING CONTACT LENSES AND STORING DEVICE

FIELD OF THE INVENTION

This invention relates to the method and system for asepticization of contact eye lenses of a wide variety of commercially known hard, soft and gas permeable lenses and the provision of means for storing asepticized lenses in such state until ready for insertion in the eye for improved vision or for cosmetic purposes.

BACKGROUND OF THE INVENTION

The present invention relates to the present applicant's prior patent, U.S. Pat. No. 4,063,890, issued Dec. 20, 1977, entitled "METHOD AND APPARATUS FOR STERILIZING AND STORING CONTACT LENSES", issued to Neville A. Baron.

As noted in applicant's prior patent, the prior art was directed toward sterilization of contact lenses by means of chemical treatment, boiling and the like, of such lenses, especially with respect to soft contact lenses which are characteristically referred to as hydrophilic lenses, owing to the presence of a substantial proportion of aqueous material in their body structure. However, the prior art appears to have had little, if any, appreciation for the need to destroy microorganisms which can be present on the surface or in the body of lenses.

Recent discoveries by applicant during the course of his professional practice as an eye physician, reveal that various patient allergies have arisen from and are traceable to the presence of various chemicals used in connection with commonly used and accepted liquid medium utilized to sterilize eye lens bodies. In addition, certain of the prior art liquid media containing seemingly harmless chemical additives or preservatives have been banned totally from use in some countries, because of their known carcinogenic causing properties.

Still further, it has been determined that most, if not all, prior art sterilization media are susceptible to micro-organism invasion and growth if not adequately protected therefrom. The foregoing health hazardous aspect of the prior art processes and liquid media illustrate only a few of the reasons for needed solutions and improvements in the field of lens body asepticization. A detailed inquiry into prior art techniques suggest a clear lack of understanding and appreciation of the seriousness of the voids and problems which exist with respect to the prior art. More, specifically, it can be readily appreciated that there is a need to provide means for asepticizing eye lens bodies which eliminate the misinterpretation by patients as to chemical and process aspects thereof.

Applicant's prior process and apparatus were primarily directed toward "soft" contact lenses and the use of ultraviolet irradiation at a wavelength longer than 221 nanometers, and preferably longer than 240 nanometers, but implicitly below the undesirable wavelength of 254 nanometers. The time duration of radiation exposure was not specifically stated, except that such exposure duration should be such as not to shorten the half-life of the polymeric soft lenses. More particularly, the prior art recognized that ultraviolet irradiation of soft lenses in their peak absorption spectrum range, i.e. 253.7 nanometers wavelength, during repeated cycles or continuous exposure for relative short periods would cause molecular deterioration thereof. In addition, the prior art appears devoid of any knowledge or appreciation for the need to destroy micro-organisms associated with contact eye lenses to thereby safeguard against diseases to the eyes or other parts of the human body which may be caused by the presence of such organisms on the surface or in the body of all lenses for the eyes, which may enter the human body through the eyes. Consequently, the focus of the prior art was solely to sterilize the lenses and their storage containers so as to avoid perceptive damage or deterioration to the contact lenses, while ignoring the very important health and possible disease aspect of the problem, which might be caused by the presence of micro-organisms not destroyed by the prior art sterilization processes and materials.

Heretofore, as noted in applicant's prior patent, it was thought in the prior art, that ultraviolet irradiation below the 254 nanometers wavelength, i.e. around 220 to 240 nanometers wavelength was the direction to go. However, after considerable research and investigation applicant has discovered the direction to go is significantly above 254 nanometers wavelength, i.e. in the 290 to 310 nanometers wavelength range. More specifically, applicant has discovered that the peak absorption spectrum of the aromatic amino acids, in particular tryptophan which is an amino acid component that is essential to growth and nutrition of micro-organisms is at about the 295 nanometers wavelength. Thus, by irradiating these organisms containing the tryptophan component it can be destroyed readily.

Applicant, after extensive investigation and research, has discovered that the absorption rate of lenses made of polymethylmethacrylate in the 290 to 400 nanometers range, is on the order of 20% to 25% which causes minimal shortening of the half-life of lenses made with these related materials. Lens which do not have this material tend to absorb energy even less in this wavelength range.

It is worth noting that all eye contact lens bodies have an inherent half-life due to their exposure to normal sunlight exposure during daily use.

As a result of these discoveries, applicant contends that an appropriate solution to the prior art problem is the use of ultraviolet irradiation spectrum in the range of 290 to 310 nanometers wavelength, so as to effectively destroy micro-organisms rapidly, as the criteria or standard for asepticization, while simultaneously avoiding any perceptive damage to a wider range of contact lenses than heretofore considered possible or realizable in the prior art.

BRIEF SUMMARY OF THE INVENTION

In accordance with the present invention, it has been discovered that it is possible to rapidly, conveniently and effectively asepticize lens bodies for contact eye lenses, including associated micro-organisms, of a wider scope of commercially used and prescribed contact lens materials than heretofore possible. More particularly, the present invention provides method and system wherein light-transmitting contact eye lenses of a wide range of material may be asepticized by the combined or synergistic effects of ultraviolet irradiation, ultrasonic vibration and chemical oxidation to destroy micro-organisms. Accordingly, during the asepticization process, the lens body oxidation liquid medium enveloping the lens and the carrier/receptacle are all asepticized without any significant damage to any of these items.

Therefore, one object of the present invention is to provide a method for asepticizing contact eye lenses adaptable to a wide range of material used for making such lenses.

Another object of the present invention is to provide a method wherein micro-organism contamination of contact lenses made of a wide range of materials can be effectively and conveniently asepticized without damage during the process.

Yet another object of the present invention is the provision of a method and system wherein the asepticization process is accomplished by the combined effects of ultraviolet irradiation, ultrasonic vibration and oxidation via free radicals produced in an aqueous liquid medium utilized in such method and system.

Still another object of the present invention is to provide ultraviolet irradiation in a preselected range of wavelengths which will be effective for destroying micro-organisms.

Yet a further object of the present invention is the provision of at least one aqueous liquid medium in which oxidation free radicals are produced when it is subjected to ultraviolet irradiation.

Still a further object of the invention is the provision of means for producing ultrasonic vibration to the contact lenses while immersed in an aqueous liquid medium to thereby cause dislodgement of micro-organisms from the surface of or within the body of the lenses during the asepticizing process.

Further, an object of the invention is the provision of process and liquid media which eliminate the need for the use of chemical additives thereby eliminating allergy and carcinogenic effects caused by the use of contact eye lens bodies and to remove any opportunity for patient misenterpretation in use of asepticizing process.

BRIEF DESCRIPTION OF THE DRAWINGS

FIG. 1 is a view in cross-section of a planar lens receptacle tray illustrating a pair of lenses immersed in an aqueous liquid medium and a cover therefor;

FIG. 2 is another view of the tray of FIG. 1, depicting the lenses therein;

FIG. 3 is a view of an apparatus enclosure for component devices contained therein which are required to perform the functions of the method in accordance with the present invention and illustrating the relative space relationship to the portable tray disposed therein.

DETAILED DESCRIPTION OF THE INVENTION

Referring now to the drawings, in FIG. 1 there is shown a portable enclosurable carrier/receptacle tray body 10 in a general planar configuration having a top surface 20 and two recesses 12 which cut through surface 20 to form plane-concave recesses. Depicted in each recess 12 is a lens body 14 disposed near the bottom of said recess. Recesses 12 contain an aqueous liquid medium 16 to a level which envelops lens body 14 while they reside in recesses 12. Recesses 12 are rendered substantially liquid-tight by a body cover 18 which is maintained in tight contact relationship with tray body 10 along to surface 20.

In FIG. 2, a top view of FIG. 1, shows the relative position of lens bodies 14 disposed in recesses 12 of tray body 10. Both tray body 10 and top cover 18 are preferably made of materials that are substantially transparent to ultraviolet irradiation wavelength in the range of 290 to 310 nanometers. For example, such material as polytetrafluoroethylene identified by the registered trademark TEFLON of DuPont, is appropriate for said tray 10 and cover 18 owing to their transparency at the preselected wavelength noted herein above and its durability as a carrier/receptacle and processing tray.

The aqueous liquid media 16 selected for use in accordance with the teachings of the present invention are characterized as being transparent to ultraviolet irradiation from the 290 nanometers wavelength and above; are campatible with ocular tissue and are also compatible with polymeric and silicone structures of the lens body materials in accordance with this invention. A variety of liquid media have been evaluated and determined to be suitable and compatible with the present inventive method. These liquid media include sterile water, sterile normal saline, sterile hydrogen peroxide of varying percent concentrations, and sterile normal saline plus solutions of methox salen. A solution containing water plus 0.9 percent sodium chloride is a saline solution.

The combination of sterile normal saline plus solutions of methox salen is considered a (suitable) medium for killing purposes because upon exposure to ultraviolet radiation, it conjugates and forms covalent bonds with the DNA of exposed micro-organisms, which lead to the formation of both monofunctional (addition to a single strand of DNA) and bifunctional adducts (cross linking of psoralen to both strands of DNA). The above reactions quickly result in static and cidal reactions to the micro-organisms exposed.

With reference to the other three liquid media, it must be understood that aromatic amino acids, a primary component of micro-organisms, are very sensitive to attack by free radicals and electrons. The foregoing explain observations in the reaction of hydroxyl radicals with the aromatic amino acids, especially tryptophan, which is considered the most reactive. The hydrogen atoms appear to react with these amino acids at rates comparable to the hydroxyl radicals. Studies on radiation-induced radicals in tryptophan in solutions indicate that the radical attack occurs almost entirely at the indole ring and reduced tryptophan radicals are formed by electron capture and hydrogen addition. Thus, the hydrated electron, hydroxyl radical and hydrogen atom can attack proteins at a number of specific locations inducing chemical changes, i.e. metabolic alteration of micro-organisms, which destroy them.

To continue, for example, when hydrogen peroxide ($H_2O_2$) is exposed to ultraviolet irradiation, it forms free radicals ($HO + H + O_2$) which are characterized as oxidation (free) radicals and do their killing of micro-organisms by metiabolic aleration. Consider further the saline solution, which is the most compatible with the human eye, also undergoes change under ionizing radiation which are particularly effective on the DNA molicule. It should be noted when peroxide is used, there should be no greater than 30 parts per million in the solution otherwise serious damage to the eye can result.

In accordance with present invention, lens body 14 may be a hard lens, such as polymethylmethacrylate for example; a soft lens or hydrogel lens, such as hydrated polyhydroxylethyl methacrylate for example; or a gaspermeable rigid lens, including cellulose acetate butyrate, siloxanyl/methacrylate, silicone resine and elastone, fluorocarbon or styrene lenses, as examples. It should be noted that all the foregoing lens materials have at least two characteristics in common, namely, critical surface tension, and ultraviolet energy absorption and inverse transmission properties.

With respect to the critical surface tension, it is that property of a lens necessary to ensure a liquid in contact with its surface, will wet such surface and spread substantially uniformly thereon. All of the lenses identified hereinabove have such critical surface tension property. It should also be noted that the various aqueous liquid media disclosed hereinabove are liquids which are compatible with lens materials disclosed. The chemistry of isotonic saline solution closely mimics that of the human tear and may be the storage fluid of choice for all contact lens in addition to being an appropriate liquid medium for the present invention.

The degree of ultraviolet energy absorption or inversely energy transmission is critical to all of the lens material disclosed for use in the present invention, in that they all tend to rapidly absorb irradiated energy up to about the 280 nanometers wavelength, and rapidly transmit such energy up to about 90% of irradiated energy between 290 to 310 nanometers wavelength range. Consequently, the lens materials disclosed herein pursuant to the present invention are substantially and rapidly damaged when exposed to ultraviolet irradiation in the range of 254 to 280 nanometers wavelength, while there is little if any, significantl damage to these lenses when they are exposed to ultraviolet irradiation in the range of 290 to 310 nanometers wavelength.

However, with respect to the micro-organisms, which are the subject of destruction in accordance with the present invention, are highly susceptible to ultraviolet energy absorption over a broad spectrum owing to their molecular makeup, i.e. the presence of aromatic amino acids containing tryptophan, whose energy absorption peaks at about the 295 nanometer wavelength, well inside the 290 to 300 nanometers wavelength range taught by the present invention.

Referring now to FIG. 3, there is shown a substantially non-ultraviolet transmission system enclosure 22 for housing the various component devices necessary to effectuate the teaching of the invention. Depicted in enclosure 22 is an ultraviolet source 24 which may be a suitable lamp containing inert gas and mercury vapor, for example, adapted to generate energy radiation in the 290 to 310 nanometers wavelength range when in the ionized state. An ultraviolet reflector 26 may be employed to enhance and focus the irradiation output energy efficiency of source 24, but is not critical to operation of the system owing to close proximity in positioning of source 24 to lens body 14 during the asepticization process. An electrical power source 28 is provided to supply the devices of the system as required. An on/off switch 30 is provided to activate the system, and an on/off illuminatable indicator 32 is provided as means for ascertaining when the system is in operation or not in operation.

Continuing, an ultrasonic vibratory means 34 is provided to impart vibratory motion to portable receptacle tray 10 containing lens body 12 and liquid medium 16 when it is inserted in system enclosure 27. The vibratory agitation of the lens body and liquid medium are deemed essential to efficient and effective destruction of micro-organisms pursuant to the disclosed invention. Also shown in FIG. 3, is a controller and timing means 36 to provide electrical control and timing signals to the various devices disposed in enclosure 22 when and where required. A substantially non-ultraviolet transmission support shelf 38 is provided for receiving the holding tray 10 in place within enclosure 22. An opening 40 in one side of enclosure 22 is provided for insertion of tray 10 prior to commencement of the asepticizing process and for removal thereof from enclosure 22 when desirable after completion of the process.

Support shelf 38 is fixedly attached to and supported by vibrator 34 and is adapted with means for retaining tray 10 in place within enclosure 22 during ultrasonic vibration of vibrator 34. It should be noted that the vibratory motion applied to tray 10 is transmitted to liquid medium 16 and lens bodies 12. This imparted vibratory action is useful for shaking microorganisms from the surface or body of the lenses so that they may be more readily attacked by the oxidation radicals in the medium and being exposed to the ultraviolet irradiation energy within the system.

Operation of the system shown in FIG. 3 is commenced by inserting tray 10 into enclosure 22, containing a pair of lenses 14 in recesses 12 enveloped in a liquid medium 16 with cover 18 tightly closed providing liquid-tight retention of the medium and lenses, through opening 40. Tray 10 is held in fixed position at a lamp-to lens body distance on the order of at least 2.54 centimeters. The lamp-to-lens spacing may be varied and is dependent upon the irradiating energy level of the ultraviolet source 24 output power and the time duration of exposure. On/off switch 30 is placed in the on-position whereupon electrical energy is fed to controller and timing means 36 which in turn determine the time duration of irradiating exposure directed through cover 18 to lens bodies 14 and liquid medium. Controller 36 is connected to ultraviolet source 24 and determines the output energy level of the ultraviolet source and also connected to vibratory source and determines the frequency of vibration for the ultrasonic source 34 along with the amplitude of such vibrations. During the asepticization process the on/off indicator 32 is illuminated.

Upon completion of the asepticization process utilizing the system arrangement shown in FIG. 3, tray 10 is removed from enclosure 22 whereupon the lenses 14 are ready and available for use immediately or they may be retained and stored in the tray immersed in the asepticized liquid medium until some later date. So long as cover 18 remains closed air-tight, lenses 14 will remain asepticized indefinitely.

The asepticizing process in accordance with present invention may be routinely performed by way of an example with the following system parameter: the vibratory frequency of ultrasonic source 34 is preferable in the range of 30 to 35 kilohertz; the ultraviolet source 24 is preferably in the range of 290 to 310 nanometers wavelength, with a minimum output of 0.3 watts continuous irradiation energy output and an ultraviolet source-to-lens spacing of at least 1.5 to 2.5 centimeters, to thereby produce an output on the order 0.854 microwatts/centimeter square at a distance of one meter for irradiation to lens bodies 14 for a period of at least one hour and preferable on the order of two hours. Processing under such parameters does not produce any significant heat effects within the system or the immediate environment. The foregoing parameters have been utilized repeatedly by applicant in asepticizing lens bodies 14 made from each of the materials disclosed herein and with all the aqueous liquid media disclosed, in various combinations of lenses and media in order to ascertain and ensure the convenience and effectiveness of the process and system in accordance with the teaching of the present invention.

In concluding, it is worth noting that the present invention advantageously solves a long standing problem of the prior art, by providing a method and system whereby a wider range of commercially available and prescribed contact eye lens materials, and storage and processing liquid media may be processed by utilizing a single system for asepticization for micro-organisms. More specifically, the process and system attacks and destroys these micro-organisms by combining the effects of ultraviolet irradiation, oxidation or chemical reactions, and vibratory action. Thus, these combined effects leave nothing to chance and eliminate patient misinterpretations regarding chemicals used or other aspects during the process and effectuates the result in a convenient method without any deteritious effects, neither chemical or mechanical, to lenses or portable receptacle.

It is to be understood that the present invention described herein is to be limited only by the scope of the teachings and the claims appended hereto. Various changes, modifications and equivalents may be substituted without departing from the spirit and scope of the invention. Thus, by way of example, the receptacle tray may be modified to hold a plurality of pairs of lenses or the ultraviolet source may be a non-ionizing gaseous source.

What is claimed as new is:

1. An improved method for destroying and rendering inert micro-organism found on the surface or in the body of a light transmitting contact lens made of polymethylmethacrylate, gas permeable or hydrogel material, comprising the steps of:
    a. immersing a contact lens in an enclosable portable receptacle containing an aqueous liquid medium; and
    b. irradiating said immersed lens, while in said enclosable receptacle and aqueous liquid medium, with ultraviolet radiation at a wavelength of approximately 290 to 310 nanometers.

2. The method of claim 1 in which said gas permeable material is cellulose acetate butyrate, siloxahyl/methacrylate, silicone resin and elastone, fluorocarbon or styrene.

3. The method of claim 1 in which said hydrogel material is hydrated polyhydroxyethyl methacrylate.

4. The method of claim 1 in which said receptacle is substantially air tight and made of polytetrafluoroethylene.

5. The method of claim 1 in which said liquid medium is sterile water, sterile normal saline, sterile hydrogen peroxide of less than 30 parts per million, or a combination of sterile normal saline and methox salen or sterile hydrogen peroxide solutions.

6. The method of claim 1 in which at least part of said receptacle is substantially transparent to ultraviolet radiation at the wavelength of said ultraviolet radiation, and in which the irradiating step is carried out by passing said ultraviolet radiation through said transparent part of the receptacle while said receptacle is closed.

7. The method of claim 1 including the step of vibrating the immersed lens in said enclosable receptacle and aqueous liquid medium at an ultrasonic frequency while carrying out the irradiating step.

8. The method of claim 7 in which said ultrasonic frequency is in the range of 30 to 35 kilohertz.

9. The method of claim 1 in which said liquid medium comprises an oxidizing agent which is broken down into free oxidation radicals when exposed to ultraviolet radiation.

10. The method of claim 9 in which said oxidizing agent is hydrogen peroxide.

11. The method of claim 9 in which said oxidizing agent is methox salen.

12. An improved system for destroying, and rendering inert, micro-organisms which may be found on the surface or in the body of a light transmitting contact lens made of polymethylmethacrylate, gas permeable or hydrogel material, the improvement comprising of:
    a. an enclosable portable carrier receptacle having a main body with a top surface with at least two recesses in said top surface of said main body, each recess being of sufficient size to accept and hold a contact lens body together with a sufficient amount of an aqueous liquid medium to envelop said contact lens body, and a substantially liquid-tight cover for enclosing said recesses; said cover, receptacle and liquid medium being substantially transparent to ultraviolet radiation at wavelengths of approximately 290 to 310 nanometers:
    b. means for radiating ultraviolet energy at wavelengths of approximately 290 to 310 nanometers, said radiating means having at least 0.3 watts of continuous energy output;
    c. means for producing ultrasonic vibrations having a frequency in the range of 30 to 35 kilohertz; and
    d. means providing an enclosure containing said ultraviolet source and maintaining said ultraviolet source in fixed, spaced relationship with said receptacle for direct irradiation of said lens body and liquid medium by said ultraviolet source through said cover, and means for receiving said receptacle in said enclosure and maintaining said receptacle in continuous vibratory contact with said means for producing ultrasonic vibrations, and electrical means, within said enclosure, for excitation and control of said means for radiating ultraviolet energy and means for producing ultrasonic vibrations.

13. An improved system of claim 12 in which said receptacle and cover are made of polytetrafluoroethylene.

* * * * *